United States Patent [19]
Reed et al.

[11] Patent Number: 6,083,978
[45] Date of Patent: Jul. 4, 2000

[54] COMPOUNDS WITH A SULFAMATE GROUP

[75] Inventors: Michael J. Reed, London; Barry V. Potter, Bath, both of United Kingdom

[73] Assignee: Sterix Limited, Oxford, United Kingdom

[21] Appl. No.: 09/142,194

[22] PCT Filed: Mar. 4, 1997

[86] PCT No.: PCT/GB97/00600

§ 371 Date: Sep. 2, 1998

§ 102(e) Date: Sep. 2, 1998

[87] PCT Pub. No.: WO97/32872

PCT Pub. Date: Sep. 12, 1997

[30] Foreign Application Priority Data

Mar. 5, 1996 [GB] United Kingdom ............... 9604709
Mar. 19, 1996 [GB] United Kingdom ............... 9605725

[51] Int. Cl.$^7$ ............... A61K 31/353; C07D 311/28; C07D 311/34
[52] U.S. Cl. ............... 514/457; 549/285; 549/278; 549/280; 549/292; 514/453; 514/455
[58] Field of Search ............... 514/453, 455, 514/457; 549/278, 280, 285, 292

[56] References Cited

U.S. PATENT DOCUMENTS

| 4,618,622 | 10/1986 | Schlecker et al. |
| 4,829,084 | 5/1989 | Bailey . |
| 6,011,024 | 1/2000 | Reed et al. |

FOREIGN PATENT DOCUMENTS

| 0 403 185 A2 | 12/1990 | European Pat. Off. |
| 2 543 140 A1 | 9/1994 | France . |
| WO 92/21353 | 12/1992 | WIPO . |
| WO 93/05064 | 3/1993 | WIPO . |

OTHER PUBLICATIONS

Nelson et al. Experienta 39 (1983), 740–742.
Pharm. Sci. (1996), 2(1), pp. 17–20 (Sahm U.G. et al.).
J. Steroid Biochem. Mol. Biol. (1995), 53 (1–6), pp. 413–420 (Reed, M.J. et al.).
J. Med. Chem. (1996), 39(7), pp. 1349–1351 (Woo, L.W.L. et al.).
J. Steroid Biochem. Mol. Biol. (1996), 57(1/2), pp. 79–88 (Woo, L.W.L. et al.).
Biochemistry (1995), 34(36), pp. 11508–11514 (Purhoit, A. et al.).
J. Med. Chem. (1994), 37(2), pp. 219–221 (Howarth, N. et al.).

*Primary Examiner*—Joseph McKane
*Assistant Examiner*—Taofiq A. Solola
*Attorney, Agent, or Firm*—Frommer Lawrence & Haug LLP; Thomas J. Kowalski

[57] ABSTRACT

A sulphamate compound suitable for use as an inhibitor of both oestrone sulphatase activity and aromatase activity. The compound can have the general formula (II) wherein F represents a phenolic ring structure (the first ring structure), J represents the third ring structure; I represents a phenolic ring structure (the second ring structure), G is an optional double bond, H is a link joining the second ring structure to the third ring structure, and Y represents a suitable second group; wherein any one of ring structures F, J and I has bound thereto a sulphamate group.

21 Claims, 7 Drawing Sheets

FIG. 1

KEY ENZYMES IN STEROIDOGENESIS:-
1. SULPHATASE  2. AROMATASE  3. DEHYDROGENASE  4. 5α REDUCTASE

FIG. 2

ORIGIN OF OESTROGENIC STEROIDS IN POSTMENOPAUSAL WOMEN

ER=OESTROGEN RECEPTOR, DHA/-S=DEHYDROEPIANDROSTERONE/-SULPHATE, ADIOL=ANDROSTENEDIOL, E1-STS=OESTRONE SULPHATASE, DHA-STS= DHA-SULPHATASE, ADIOL-STS=ADIOL SULPHATASE, 17B-HSD=OESTRADIOL 17B-HYDROXYSTEROID DEHYDROGENASE

III

FIG. 7 VII

FIG. 8 VIII

COMPOUNDS WITH A SULFAMATE GROUP

RELATED APPLICATIONS

This application is in the National Phase under 35 U.S.C. §371 of PCT/GB97/00600, filed Mar. 4, 1997.

The present invention relates to a compound.

In particular the present invention relates to a pharmaceutical composition comprising the compound.

Breast and endometrial cancers are major causes of death in Western women. In particular, tumours in endocrine-dependent tissues, such as the breast and endometrium, occur most frequently in postmenopausal women at a time when the ovaries have ceased their production of oestrogens.

Evidence suggests that oestrogens are the major mitogens involved in stimulating and promoting the growth of tumours in endocrine-dependent tissues, such as the breast and endometrium[21]. Although plasma oestrogen concentrations are similar in women with or without breast cancer, breast tumour oestrone and oestrone levels are significantly higher than in normal breast tissue or blood. In addition, in postmenopausal women oestrogens continue to be produced by extraglandular production in adipose tissue but also in normal and malignant breast tissues[22].

Figure 1:
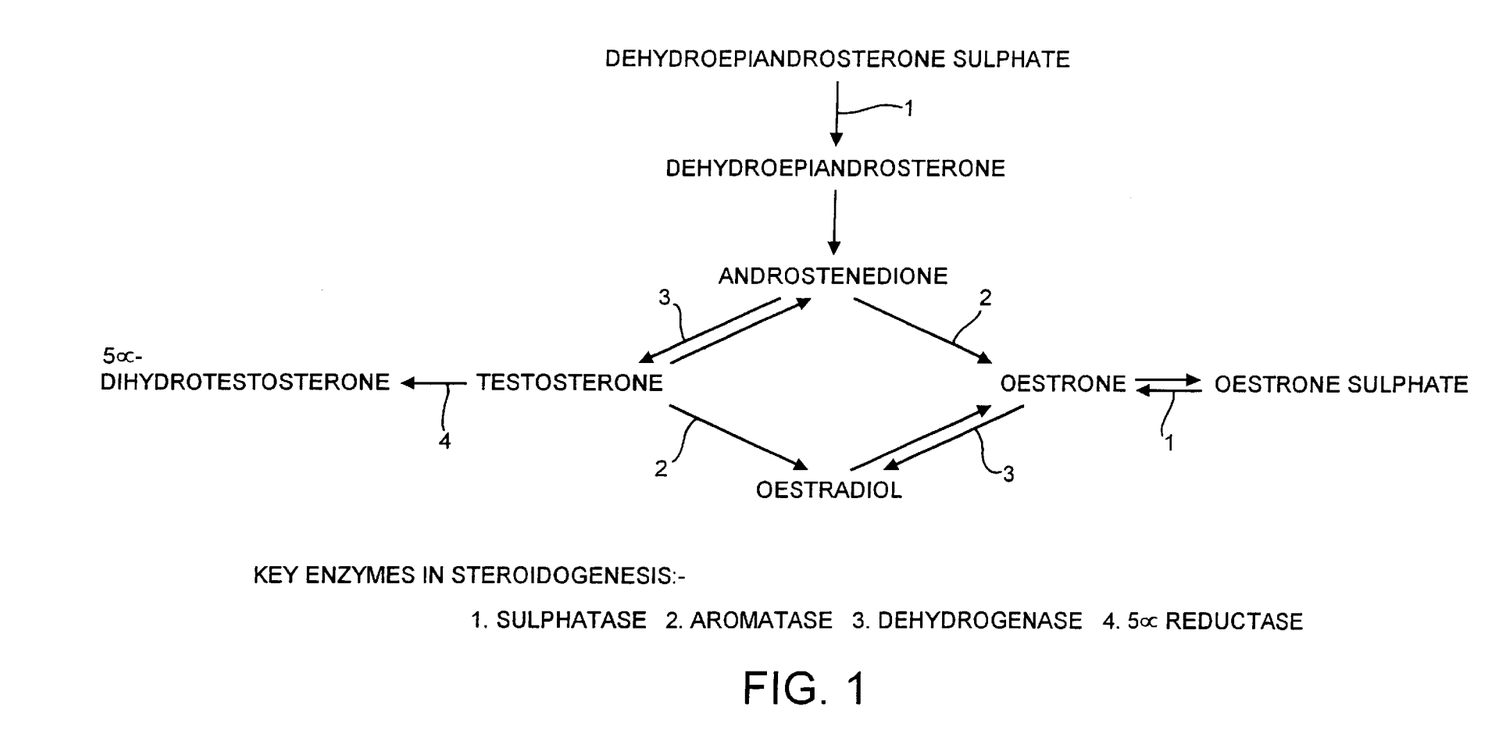
FIGS. 1 and 2 present schematic pathways.
Figure 2:
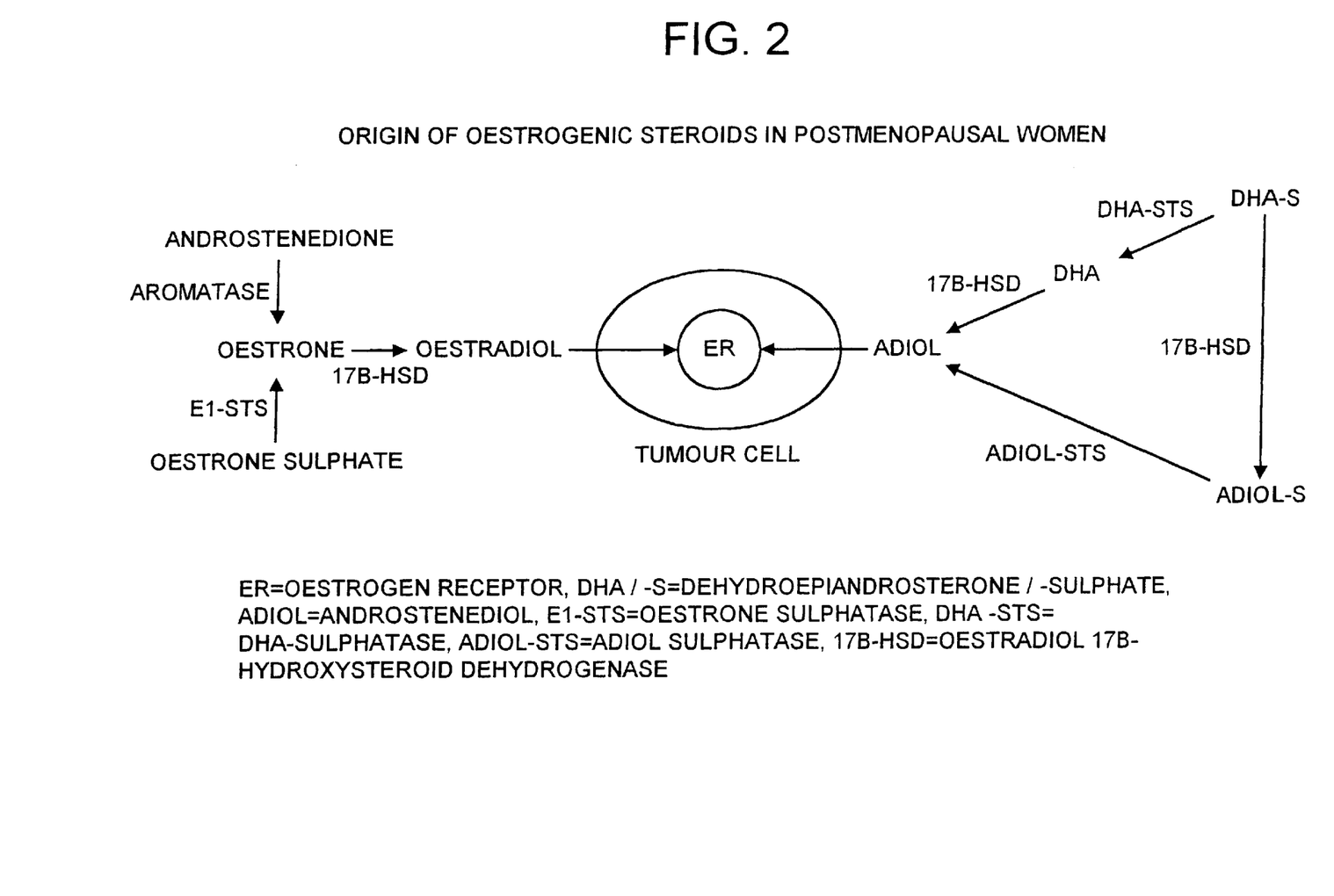

FIGS. 1 and 2 are schematic diagrams showing some of the enzymes involved in the in situ synthesis of oestrone from oestrone sulphate, oestradiol and androstenedione.

In FIG. 2, which schematically shows the origin of oestrogenic steroids in postmenopausal women, "ER" denotes Oestrogen Receptor, "DHA/-S" denotes Dehydroepiandrosterone/-Sulphate, "Adiol" denotes Androstenediol. "E1-STS" denotes Oestrone Sulphatase, "DHA-STS" denotes DHA-sulphatase, "Adiol-STS" denotes Adiol Sulphatase, and "17B-HSD" denotes Oestradiol 17B-hydroxysteroid dehydrogenase.

As can be seen, the main two enzymes that are involved in the peripheral synthesis of oestrogens are the aromatase enzyme an the enzyme oestrone sulphatase.

In short, the aromatase enzyme converts androstenedione, which is secreted in large amounts by the adrenal cortex, to oestrone. Recent reports have suggested that some flavones could inhibit aromatase activity[35,36].

Much of the oestrone so formed, however, is converted to oestrone sulphate (E1S) and there is now a considerable body of evidence showing that E1S in plasma and tissue acts as a reservoir for the formation of oestrone by the action of oestrone sulphatase[23].

In this regard, it is now believed that the oestrone sulphatase (E1-STS) pathway—i.e. the hydrolysis of oestrone sulphate to oestrone (E1S to E1) is the major source of oestrogen in breast tumours[1,2]. This theory is supported by a modest reduction of plasma oestrogen concentration in postmenopausal women with breast cancer treated by aromatase inhibitors, such as aminoglutethimide and 4-hydroxyandrostenedione[3,4] and also by the fact that plasma E1S concentration in these aromatase inhibitor-treated patients remains relatively high. The Ion half-life of E1S in blood (10–12 h) compared with the unconjugated oestrogen (20 min)[5] and high levels of steroid sulphatase activity in liver and, normal and malignant breast tissues, also lend support to this theory[6].

Thus, oestrogen formation in malignant breast and endometrial tissues via the sulphatase pathway makes a major contribution to the high concentration of oestrogens which are present in these tumours[24,25].

PCT/GB92/01587 teaches novel steroid sulphatase inhibitors and pharmaceutical compositions containing them for use in the treatment of oestrone dependent tumours, especially breast cancer. These steroid sulphatase inhibitors are sulphamate esters, such as N,N-dimethyl oestrone-3-sulphamate nd, preferably, oestrone-3-sulphamate (otherwise known as "EMATE").

EMATE is a potent E1-STS inhibitor as it displays more than 99% inhibition of E1-STS activity in intact MCF-7 cells at 0.1 μM. EMATE also inhibits the E1-STS enzyme in a time-dependent and concentration-dependent manner, thereby indicating that it acts as an active site-directed inactivator[7,3].

Although EMATE was originally designed for the inhibition of E1-STS, it also inhibits dehydroepiandrosterone sulphatase (DHA-STS), which is an enzyme that is believed to have a pivotal role in regulating the biosynthesis of the oestrogenic steroid androstenediol[8,9]. This is of significance as there is now evidence to suggest that androstenediol may be of even greater importance as a promoter of breast tumour growth[10].

EMATE is also active in vivo as almost complete inhibition of rat liver E1-STS (99%) and DHA-STS (99%) activities resulted when it is administered either orally or subcutaneously[11]. In addition, EMATE has been shown to have a memory enhancing effect in rats[14]. Studies in mice have suggested an association between DHA-STS activity and the regulation of part of the immune response. It is thought that this may also occur in humans[15,16]. The bridging O-atom of the sulphamate moiety in EMATE is believed to be important for inhibitory activity. Thus, when the 3-O-atom is replaced by other heteroatoms—as in oestrone-3-N-sulphamate and oestrone-3-S-sulphamate—these analogues are weaker non-time-dependent inactivators[12].

Thus, EMATE is a potent steroid sulphatase inhibitor which blocks the hydrolysis of both E1S and DHA-S[29-31]. This inhibitor, therefore, not only blocks the synthesis of oestrone from E1S but also the formation of androstenediol from DHA-S.

In addition to oestrone, the other major steroid with oestrogenic properties which is produced by postmenopausal women is androstenediol (see FIG. 2).

Androstenediol, although an androgen, can bind to the oestrogen receptor (ER) and can stimulate the growth of ER positive breast cancer cells and the growth of carcinogen-induced mammary tumours in the rat[26,27]. Importantly, in postmenopausal women 90% of the androstenediol produced originates from the androgen dehydroepiandrosterone sulphate (DHA-S) which is secreted in large amounts by the adrenal cortex. DHA-S is converted to DH by DHA sulphatase, which may be the same as, or different from, the enzyme, oestrone sulphatase, which is responsible for the hydrolysis of E1S[28].

During the last 10–15 years considerable research has also been carried out to develop potent aromatase inhibitors, some of which are currently undergoing clinical evaluation. However, in three recent reports of postmenopausal women with breast cancer who received aromatase inhibitor therapy, plasma E1S concentrations remained between 400–1000 pg/ml[32-34].

In summation therefore in situ synthesis of oestrogen is thought to make an important contribution to the high levels of oestrogens in tumours and therefore specific inhibitors of oestrogen biosynthesis are of potential value for the treatment of endocrine-dependent tumours.

Moreover, even though oestrogen formation in malignant breast and endometrial tissues via the sulphatase pathway makes a major contribution to the high concentration of oestrogens, there are still other enzymatic pathways that contribute to in vivo synthesis of oestrogen.

Thus, there is an urgent need to develop new therapies for the treatment of these cancers.

The present invention therefore seeks to overcome one or more of the problems associated with the prior art methods of treating breast and endometrial cancers.

According to a first aspect of the present invention there is provided a sulphamate compound suitable for use as an inhibitor of both oestrone sulphatase activity and aromatase activity.

In a highly preferred embodiment, the compound of the present invention is a non-steroidal compound.

According to a second aspect of the present invention there is provided a compound having the general formula II wherein F represents a phenolic ring structure (a first ring structure), J represents a third ring structure, I represents a phenolic ring structure (a second ring structure), G is an optional double bond, H is a link joining the second ring structure to the third ring structure, and Y represents a suitable second group; wherein any one of ring structures F, J and I has bound thereto a sulphamate group.

According to a third aspect of the present invention there is provided a compound according to the present invention for use as pharmaceutical.

According to a fourth aspect of the present invention there is provided a compound according to the present invention for inhibiting oestrone sulphatase activity and aromatase activity.

According to a fifth aspect of the present invention there is provided a pharmaceutical composition comprising a compound according to the present invention; and a pharmaceutically acceptable carrier, excipient or diluent.

According to a sixth aspect of the present invention there is provided the use of a compound according to the present invention in the manufacture of a pharmaceutical for inhibiting oestrone sulphatase activity and aromatase activity.

According to a seventh aspect of the present invention there is provided a process for preparing a compound according to the present invention, the process comprising sulphating a flavone, isoflavone or a flavanone.

According to an eighth aspect of the present invention there is provided a process for preparing a compound according to the present invention, the process comprising sulphamoylating a flavone, isoflavone or a flavanone.

In one aspect, therefore, the present invention provides a compound, or a pharmaceutical composition comprising the same that can affect, such as substantially inhibit, not only the oestrone sulphatase path—which pathway converts oestrone to and from oestradiol—but also the aromatase pathway—which pathway converts the androgen precursor androstenedione to oestrone.

This aspect of the present invention is advantageous because by the administration of one type of compound it is possible to block the synthesis of oestrone from both androstenedione and E1S.

In addition, the present invention is further advantageous in that it may also be possible to block the formation of androstenediol from DHA-S.

Hence, the present invention provides compounds that have considerable therapeutic advantages, particularly for treating breast and endometrial cancers.

The compounds of the present invention are different from those disclosed in the prior art because they can act as therapeutic agents that possess both aromatase and steroid sulphatase inhibitory properties.

In a preferred embodiment the compound of the present invention comprises a first ring structure and a sulphamoyl group, which first ring structure may be substituted and/or unsaturated.

Preferably the first ring structure is a phenolic ring structure, which phenolic ring may be substituted.

Preferably, the compound of the present invention further comprises a second ring structure, which second ring structure may be substituted and/or unsaturated.

Preferably the second ring structure is a phenolic ring structure, which phenolic ring may be substituted.

Preferably, the compound of the present invention further comprises a third ring structure which is intermediate the first ring structure and the second ring structure, which third ring structure may be substituted and/or unsaturated.

Figure 10:
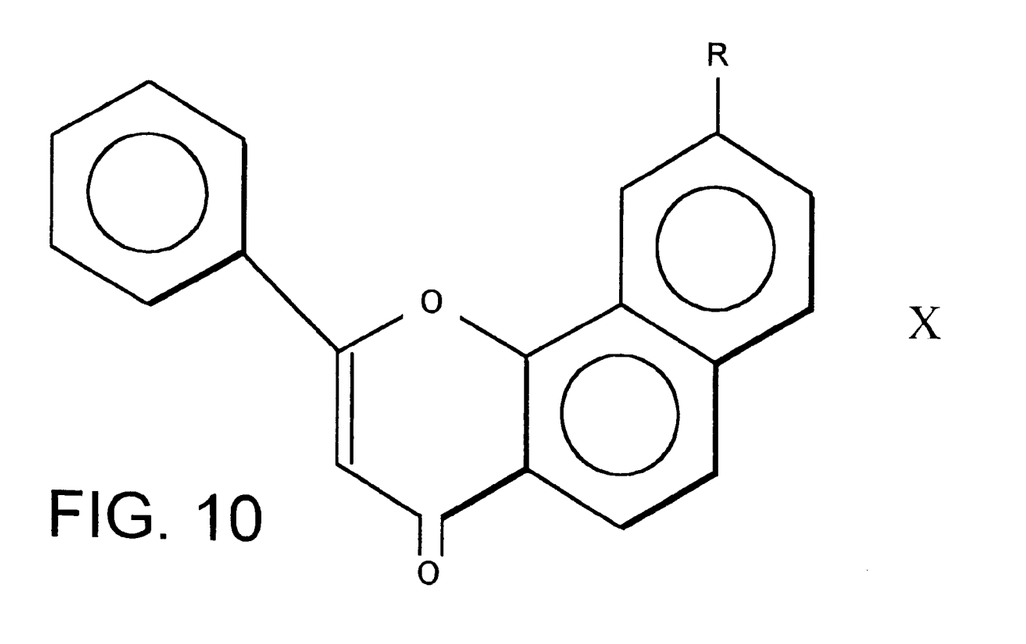

In a prefered embodiment, the compound of the present invention is a sulphamate of a flavone, an isoflavone or a flavanone. Alternatively, the compound of the present invention is a sulphamate of a benzoflavone—such as the benzoflavone of FIG. 10 wherein R is H or OH (ref. 38). The present invention also covers substituted variants of the sulphamate of the benzoflavone of FIG. 10.

The present invention will now be described by reference to the Formulae presented in FIGS. 3–9.

In this regard, its is generally preferred that the compound of the present invention has the general formula I wherein A represents the first ring structure, B represents the third ring structure, D represents the second ring structure, C is an optional double bond, E is a link joining the second ring structure to the third ring structure, X represents a suitable first group, and Y represents a suitable second group; wherein any one of ring structures A, B and D is a phenolic ring; and wherein any one of ring structures A, B and D has bound thereto a sulphamate group.

Each of the ring structures can independently comprise from 3 to 20 atoms in the ring, preferably from 4 to 8 atoms in the ring. Preferably, ring A and ring D comprise 6 atoms in the ring.

A further cyclic group may be linked to ring A or D. This cyclic group may be linked to two spaced-apart atoms in ring A or ring D, such as the structure shown in FIG. 10.

Preferably, the first ring structure and the second ring structure are substituted.

Preferably, any one of ring structures A and D has bound thereto a sulphamate group.

Preferably, each of the first ring and the second ring is a homogeneous ring structure—i.e. the ring is made up of the same atoms.

Preferably, each of the first ring and the second ring comprises only carbon atoms in the ring.

Preferably, X is C=O.

Figure 3A:
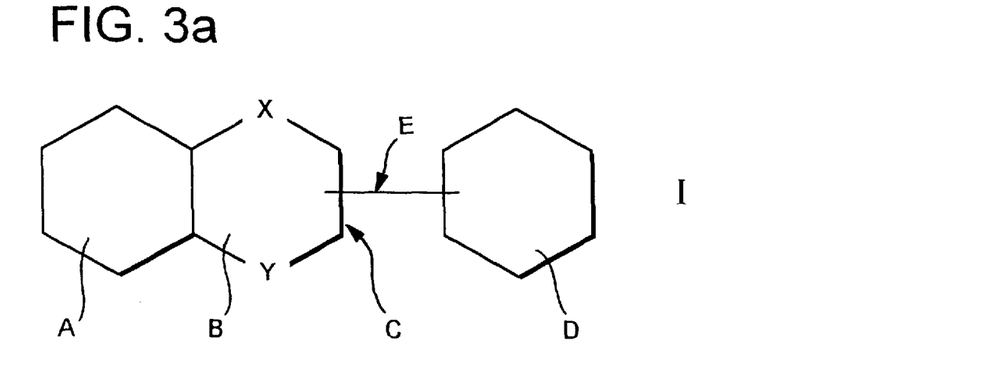
FIGS. 3–10 present chemical formulae.
Figure 3B:
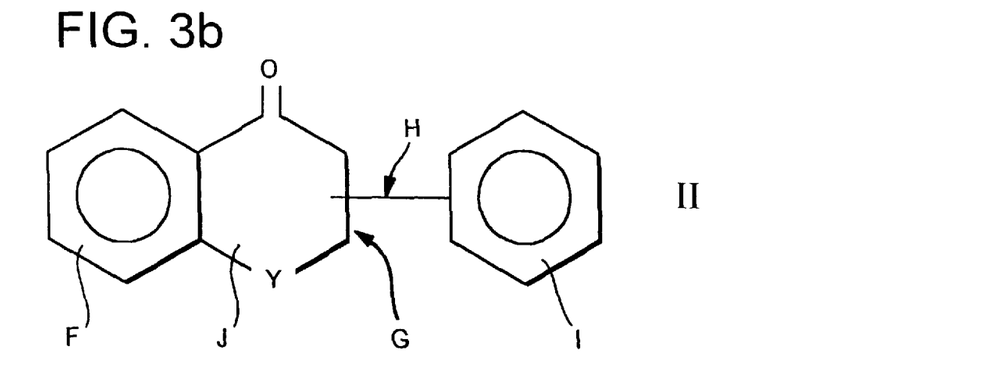

Preferably, the compound of the present invention has the general formula II wherein F represents a phenolic ring structure (the first ring structure), J represents the third ring structure, I represents a phenolic ring structure (the second ring structure), G is an optional double bond, H is a link joining the second ring structure to the third ring structure, and Y represents a suitable second group; wherein any one of ring structures F, J and I has bound thereto a sulphamate group.

Preferably, the third ring structure is a heterogeneous ring structure—i.e. different atoms are in the ring.

Preferably, Y is O.

Preferably any one of the ring structures F and I has bound thereto a sulphamate group.

Preferably, link E or link H is a bond.

Preferably, the compound of the present invention is a sulphamate of any one of a flavone, an isoflavone or a flavanone.

Figure 4:
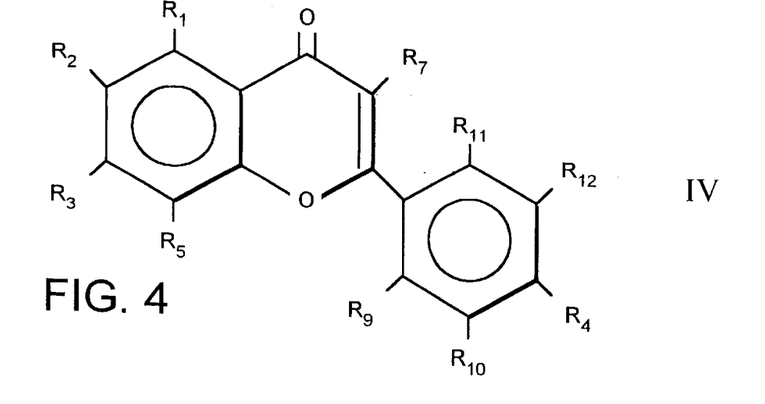
Figure 5:
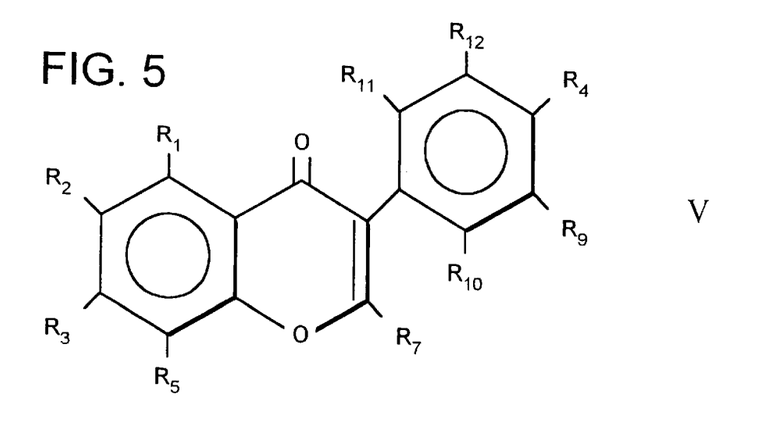
Figure 6:
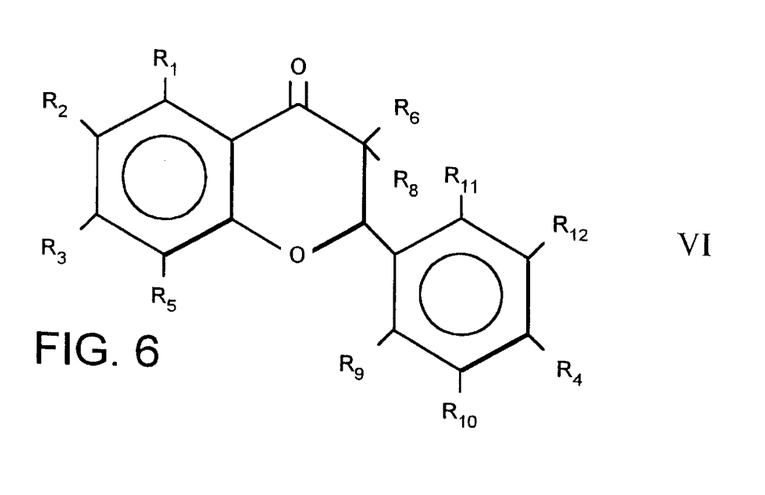

Preferably, the compound of the present invention is any one of a compound of the general formula IV, a compound of the gene formula V, or a compound of the general formula VI; wherein $R_1$–$R_{12}$ are independently selected from H, OH, a halogen, an amine, an amide, a sulphonamine, a sulphonamide, any other sulphur containing group, a saturated or unsaturated $C_{1-10}$ alkyl, an aryl group, a saturated or unsaturated $C_{1-10}$ ether, a saturated or unsaturated $C_{1-10}$ ester, a phosphorus containing group; and wherein at least one of $R_1$–$R_{12}$ is a sulphamate group.

Preferably, the sulphamate group has the genera formula $OSO_2NR_{13}R_{14}$ wherein $R_{13}$ and $R_{14}$ are independently selected from H, OH, a halogen, a saturated or unsaturated $C_{1-10}$ alkyl, an aryl group, a saturated or unsaturated $C_{1-10}$ ether, a saturated or unsaturated $C_{1-10}$ ester. Each of $R_{13}$ and $R_{14}$ may be other suitable groups.

Preferably, the compound of the present invention is any one of a compound of the general formula IV, a compound of the general formula V, or a compound of the general formula VI; wherein $R_1$–$R_{12}$ are independently selected from H, OH, $OSO_2NR_{13}R_{14}$, O—$CH_3$; wherein at least one of $R_1$–$R_{12}$ is $OSO_2NR_{13}R_{14}$, and wherein $R_{13}$ and $R_{14}$ are defined as above.

Preferably, at least one of $R_{13}$ and $R_{14}$ is H. Preferably, each of $R_{13}$ and $R_{14}$ is H.

Figure 7:
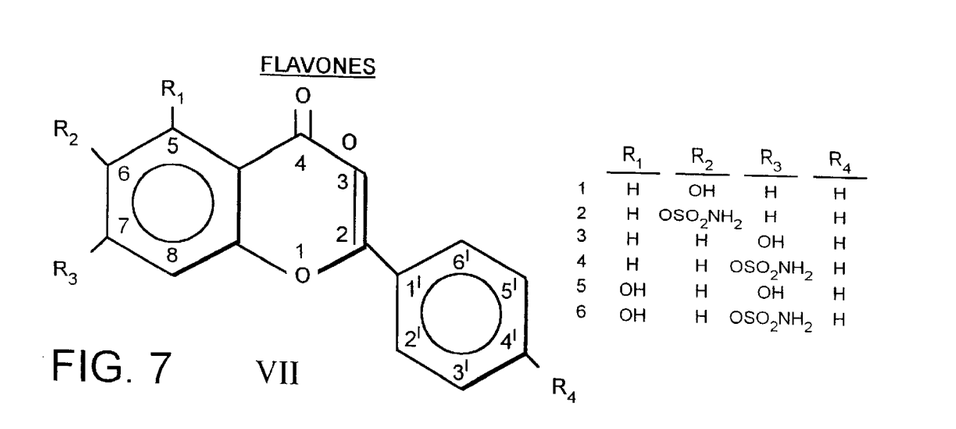
Figure 8:
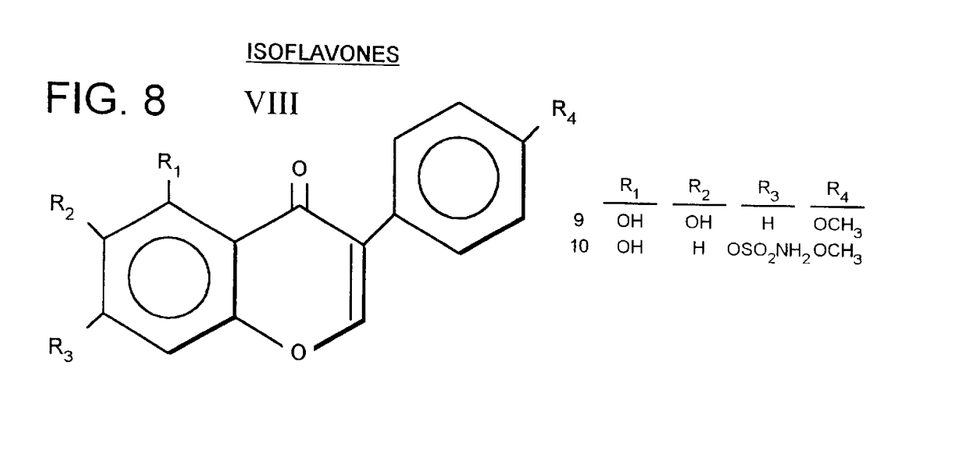
Figure 9:
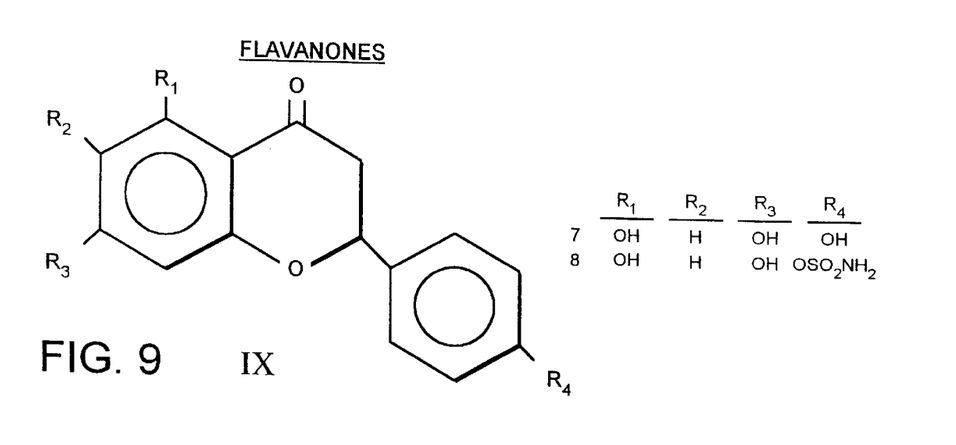

Preferably, the compound of the present invention is a sulphamate of any one of the flavone of formula VII, the isoflavone of formula VIII, or the flavanone of formula IX.

Preferably, the compound of the present invention is the sulphamate of any one of formula VII, formula VIII or formula IX.

Figure 3C:
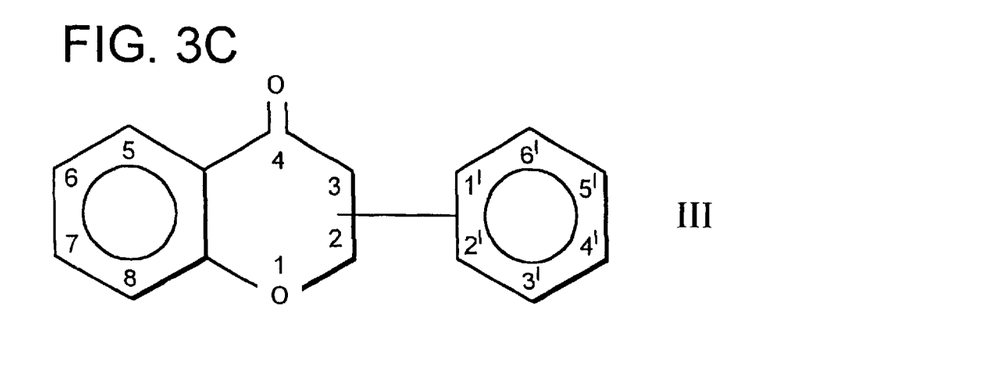

Preferably, the compound of the present invention is a sulphamate of any one of a flavone, an isoflavone or a flavanone; and wherein the sulphamoyl group is on the C4' atom of the flavone, isoflavone or flavanone. The C4' position has been shown in general Formula III according to the present invention.

Preferably, the compound of the present invention is a flavonoid or flavanoid sulphamate.

In summation the present invention provides compounds that avoid the need for polytherapy. In this regard, the compounds of the present invention can act as therapeutic agents that possess both aromatase and steroid sulphatase inhibitory properties.

Preferably, if the sulphamate group of the compound of the present invention were to be replaced with a sulphate group so as to form a sulphate compound then that sulphate compound would be hydrolysable by an enzyme having steroid sulphatase (E.C. 3.1.6.2) activity.

BRIEF DESCRIPTION OF THE DRAWINGS

The compound of the present invention may have one or more sulphamate groups. For example, the compound may be a mono-sulphamate or a bis-sulphamate. For example, in FIGS. 7, 8 and 9 $R_3$ and $R_4$ may be each a sulphamate.

The present invention will now be described only by way of example.

Compounds Synthesised

The following sulphamate derivatives were synthesised from the following parent compounds:

| PARENT COMPOUND | SULPHAMATE COMPOUND |
|---|---|
| 1 | 2 |
| 3 | 4 |
| 5 | 6 |
| 7 | 8 |
| 9 | 10 | wherein

1 = 6-hydroxy flavone
2 = flavone-6-sulphamate
3 = 7-hydroxy flavone
4 = flavone-7-sulphamate
5 = 5,7-dihydroxy flavone
6 = 5-hydroxy-flavone-7-sulphamate
7 = 5,7-dihydroxy-4'-hydroxy-flavone
8 = 5,7-dihydroxy flavanone-4'-flavanone sulphamate
9 = 5,7-dihydroxy-4'-methoxy-isoflavone
10 = 5-hydroxy-4'-methoxy-isoflavone-isoflavone-7-sulphamate The formulae are presented in FIGS. 7–9.

Synthesis

The sulphamate derivatives were prepared essentially as described previously[29]. In this regard, a solution of the appropriate flavone, isoflavone or flavanone in anhydrous DMF was treated with sodium hydride (60% dispersion; 1 equiv for 2 and 4; 2 equiv for 6, 8 and 10) at 0° C. under an atmosphere of $N_2$. After evolution of hydrogen had ceased, sulfamoyl chloride (2 equiv for 8, 5 equiv) was added and the reaction mixture was poured into brine after warming to room temperature overnight and diluting with ethyl acetate. The organic fraction was washed exhaustively with brine, dried ($MgSO_4$), filtered and evaporated. The crude product obtained was purified by flash chromatography and recrystallisation to give the corresponding sulfamate.

Flavone 6-O-sulphamate (2)

6-Hydroxyflavone (1.0 g, 4.113 mmol) gave crude product (1.21 g) which was fractionated on silica (200 g) with ethyl acetate. Upon evaporation, the first fraction gave a creamy residue (760 mg, 58.2%) which was recrystallised in warm acetone/hexane (3:2) to give 2 as creamy rod-shaped crystals (557 mg), m.p. 190–191° C.; $R_f$s=0.71 (ethyl acetate), 0.51 (ethyl acetate/hexane, 2:1), vmax (KBr) 3260, 3040, 1620, 1600, 1580, 1370, 1180 $cm^{-1}$; $\delta_H$ (acetone-$d_6$) 6.917 (1H, s, C-3-H), 7.355 (2H, br s, exchanged with $D_2O$, —$OSO_2NH_2$), 7.64 (3H, m, C-3'-H, C-4'-H and C-5'-H), 7.75 (1H, dd, $J_{C-8-H, C-7-H}$32 9 Hz and $J_{C-5-H, C-7-H}$=3Hz, C-7-H), 7.87 (1H, d, $J_{C-7-H, C-8-H}$=9Hz, C-8-H), 8.02 (1H, d, $J_{C-7-H, C-5-H}$=3Hz, C-5-H) and 8.13 (2H, m, C-2'-H and C-6'-H). MS: m/z (E.I. rel. intensity) 317.0(11), 304.2(6), 238.0(96), 210.0(16), 187.1(14), 152.0(8). 136.0(100). Acc. MS (E.I.): m/z 317.0296, $C_{15}H_{11}NO_5S$ requires 317.0358. Found C, 56.7; H, 3.44; N, 4.31. $C_{15}H_{11}NO_5S$ requires C, 56.78; H, 3.49; N, 4.41%.

Flavone 7-O-sulphamate (4)

7-Hydroxyflavone (700 mg, 2.938 mmol) gave crude product (770 mg) which was fractionated on silica (200 g) with ethyl acetate. Upon evaporation, the first fraction gave a light brown residue (132 mg) which was recrystallised in hot isopropyl alcohol to give 4 as white needle-shaped crystals (60 mg), m.p. 172–174° C. (dec.); $R_f$s=0.78 (ethyl acetate), 0.56 (ethyl acetate/hexane, 4:1); vmax (KBr) 3260, 3100, 1630, 1600, 1400, 1580, 1200, 1150 cm$^{-1}$; $\delta_H$ (DMSO-d$_6$/CDCl$_3$, ca. 1:20) 6.824 (1H, s, C-3-H, 7.396 (1H, dd, $J_{C-5-H, C-6-H}$=8.8 Hz and $J_{C-8-H, C-6-H}$=2.2 Hz, C-6-H, 7.47 (2H, br s, exchanged with D$_2$O, —OSO$_2$NH$_2$), 7.55 (3H, m, C-3'-H, C-4'-H and C-5'-H), 7.639 (1H, d, $J_{C-6-H, C-8-H}$=2.2 Hz, C-8-H), 7.92 (2H, m, C-2'-H and C-6'-H) and 8.220 (1H, d, $J_{C-6-H, C-5-H}$=8.8 Hz, C-5-H). Found: C, 56.5; H, 3.36; N, 4.19. $C_{15}H_{11}NO_5S$ requires C, 56.78; H, 3.49; N, 4.41%.

5-Hydroxyflavone 7-O-Sulphamate (6)

5,7-Dihydroxyflavone (1,0 g, 3.933 mmol) gave crude product (1.13 g) which was fractionated on silica (200 g) with chloroform/acetone (8:1). Upon evaporation, the second fraction gave a yellow residue (324 mg, 24.7%) which was recrystallised in ethyl acetate/hexane (1:1) to give 6 as yellow crystals (213 mg), m.p. 195–200° C. (dec.); $R_f$s= 0.21, 0.25 and 0.44 for chloroform/acetone 12:1, 8:1 and 4:1 respectively; vmax (KBr) 3360, 3250, 2925–2850, 1650, 1610, 1380 cm$^{-1}$, $\delta_H$ (acetone-d$_6$) 6.75, 6.98, 7.17 (3H, three s, C3-H, C-6-H, C-8-H), 7.63 (2H, br s, exchanged with D$_2$O, —OSO$_2$NH$_2$), 7.65 (3H, m, C-3'-H, C-4'-H and C-5'-H), 8.15 (2H, d, J=7.7 Hz, C-2'-H and C-6'-H) an 13.0 (1H, br s, exchanged with D$_2$O, C-5-OH). MS: m/z (+ve ion FAB in m-NBA, rel. intensity) 440.1(10), 389.3(10), 334.1[100, (M+H)$^+$], 288.1(17), 255.0[25, (M+H−79)$^+$], 169.1(30). MS: m/z (−ve ion FAB in m-NBA, rel. intensity) 499.0(30), 484.1[14, (M−2H+153)$^-$], 475.1(20), 443.1(24), 332.1[100, (M−H)$^-$], 308.1(28) 274.1(20), 253.1[50, (M−H−79)$^-$], 195.1(24). Acc. MS (+ve ion FAB in m-NBA): m/z 334.0392, $C_{15}H_{12}NO_6S$ requires 334.0385. Found: C, 54.0; H, 3.39; N, 4.21. $C_{15}H_{11}NO_6S$ requires C, 54.03; H, 3.33; N, 4.20%.

5,7-Dihydroxyflavanone 4'-O-sulphamate (8)

4',5,7-Trihydroxyflavanone (1.0 g, 3.675 mmol) gave crude product (965 mg) which was fractionated on silica (200 g) with ethyl acetate/hexane (4:1) to give a mixture of the starting flavanone and product. This mixture was further fractionated on silica (200 g) with chloroform/acetone (4:1) and upon evaporation, the second fraction gave a pale yellow oil (345 mg, 34%) which solidified on standing. Subsequent recrystallisation of this solid in ethyl acetate/hexane (1:1) gave 8 as white crystals (259 mg), m.p. 211–213° C.; $R_f$=0.21 (chloroform/acetone, 4:1); vmax (KBr) 3420, 3340, 3260, 3140, 1640, 1510, 1380, 1160 cm$^{-1}$; $\delta_H$ (acetone-d$_6$) 2.84 (1H, dd, $J_{AB}$=17.4 Hz and $J_{ax, eq}$=3.1 Hz, C-3-H$_B$), 3.19 (1H, dd, $J_{BA}$=16.9 Hz and $J_{ax, ax}$=12.8 Hz, C-3-H$_A$), 5.62 (1H, dd, $J_{ax, eq}$=3.1 H and $J_{ax, ax}$=12.8 Hz, C-2-H), 5.98 (1H, d, J=2.0 Hz, C-6-H or C-8-H), 6.01(1H, d, J=2.0 Hz, C-6-H or C-8-H), 7.20 (2H, br s, exchanged with D$_2$O, —OSO$_2$NH$_2$), 7.40 (2H, d, J=8.7 Hz, C-2'-H and C-6'-H), 7.66 (2H, d, J=8.7 Hz, C-3'-H and C-5'-H), 9.65 (1H, br s, C-7-OH) and 12.15 (1H, s, C-5-OH). MS: m/z (+ion FAB in m-NBA, rel. intensity) 352.0[100, (M+H)$^+$], 288.1(10), 272.1[14, (M−79)$^-$], 255.2(9), 169.0 (13). MS: m/z (−ve ion FAB in m-NBA, rel. intensity) 701.2(12) 606.2(10), 517.1(42), 504.1[20, (M+153)$^-$], 473.2 (10), 350.1[100, (M−H)$^-$], 271.1[45, (M−H−79)$^-$], 182.0(8). Acc. MS (+ve ion FAB in m-NBA): m/z 352.0496, $C_{15}H_{14}NO_7S$ requires 352.0491. Found: C, 51.1; H, 3.68; N, 3.98. $C_{15}H_{13}NO_7S$ requires C, 51.28: H, 3.73; N, 3.99%.

5-Hydroxy-4'-methoxyisoflavone 7'-O-sulphamate (10)

5,7-Dihydroxy-4'-methoxyisoflavone (800 mg, 2.817 mmol) gave crude product (650 mg) which was fractionated on silica (200 g) with chloroform/acetone (8:1). Upon evaporation, the second fraction gave a yell residue (266 mg, 26%) which was recrystallised in ethyl acetate/hexane (1:1) to give 10 as yellow crystals (211 mg), m.p. 184–188° C.; $R_f$s=0.22 and 0.59 or chloroform/acetone 8:1 and 4:1 respectively; vmax (KBr) 3300–3020, 1660, 1610, 1400 cm$^{-1}$; $\delta_H$ (acetone-d$_6$) 3.86 (3H, s, —OCH$_3$), 6.75 (1H, d, J=2.2 Hz, C-6-H or C-8-H), 7.04 (3H, m, C-6-H or C-8-H and C-3'-H and C-5'-H), 7.49 (2H, br s, exchanged with D$_2$O, —OSO$_2$NH$_2$), 7.58 (2H, d, J=7 Hz, C-2'-H and C-6'-H), 8.41 (1H, s, C-2-H), 13.05 (1H, br s, exchanged with D$_2$O, C-5-OH). MS: m/z (+ve ion FAB in m-NBA, ret. intensity) 393.3(12), 364.0[100, (M+H)$^+$], 284.1[12, (M−79)$^+$], 169.1 (24), 134.0(22). MS: m/z (−ve ion FAB in m-NBA, rel. intensity) 529.1(25), 515.1[12, (M−H+153)$^-$], 442.1(20), 362.1[100, (M−H)$^-$], 308.1(34), 283.1[70, (M−H−79)$^-$], 170.1(26). Acc. MS (+ve ion FAB in m-NBA): m/z 364.0494, $C_{16}H_{14}NO_7S$ requires 364.0491. Found: C, 52.8; H, 3.65; N, 3.81. $C_{16}H_{13}NO_7S$ requires C, 52.89; H, 3.61; N, 3.85%.

5-Hydroxy Isoflavone-4',7-O,O-Disulphamate (11) and 5,7-Dihydroxy Isoflavone-4'-O-Sulphamate (12)

4',5,7-Trihydroxy isoflavone (0.5 g, 1.85 mmol) upon sulphamoylation gave a crude product (0.65 g) which was fractionated on silica (200 g) with chloroform/acetone (4:1), and upon evaporation the third fraction gave a light yellow residue (0.329 g, 51%) which was recrystallized in ethylacetate/hexane (1:2) to give compound (11) as beige crystals (0.197 g); m.p=>198° C. (dec); $R_f$s=0.14 and 0.24 for chloroform/acetone 4:1 and 2:1 respectively; $v^{max}$ (KBr) 3460 (—NH$_2$), 1650 (C=O), 1400 (—SO$_2$N—) cm$^{-1}$; $\delta_H$ (acetone-d$_6$) 6.78 (1H, d J=2.2 Hz, C-6-H or C-8-H, 7.03 (1H, d, J=2.2 Hz, C-8-H or C-6-H), 7.4 (4H, br s, exchanged with D$_2$O, C4'-OSO$_2$NH$_2$ and C-7-OSO$_2$NH$_2$), 7.43 (2H, d, J=8.4 Hz, C-3'-H and C-5'-H or C-2'-H and C-6'-H and C-6'-H), 7.72 (2H, d, J=8.4 Hz, C-2'-H and C-6'-H or C-3'-H and C-5'-H), 8.51 (1H, s, C-2-H) and 12.93 (1H, s, C-5-OH). MS: m/z (+ve ion FAB in m- NBA, rel. intensity) 28.9 [100, (M+H)$^+$], 350.0 [20, (M+H—SO$_2$NH$_2$)$^+$], 272.1 [30, (M−H—SO$_2$NH$_2$)$^+$]. MS: m/z (−ve ion FAB in m-NBA, rel. intensity) 426.9 [100, (M−H)$^-$], 347.9 [95, (M−H—SO$_2$NH$_2$)$^-$], 269.0 [30, (M−H—SO$_2$NH$_2$)$^-$]. Acc. MS: m/z (FAB)$^+$429.0083 $C_{15}H_{13}N_2O_9S_2$ requires 429.0063. Found C, 42.0; H, 2.91; N, 6.45; $C_{15}H_{12}N_2O_9S_2$ requires C, 42.06; H, 2.82; N, 6.54%.

The second fraction was collected and upon evaporation gave light yellow residue (0.112 g, 17%) which was recrystallized in ethylacetate/hexane (1:3) to give compound (12) as pale white crystals (0.068 g); m.p.=189–192° C. $R_f$s=0.23 and 0.33 for chloroform/acetone 4:1 and 2:1 respectively; $v^{max}$ (KBr) 3500–3300 (—NH$_2$), 3200 (H-bonded-OH), 1680 (C=O), 1610, 1400 (—SO$_2$N—)cm$^{-1}$; $\delta_H$ (acetone-d$_6$) 6.32 (1H, d, J=2.2 Hz, C-6-H or C-8-H), 6.46 (1H, d, J=2.2 Hz, C-8-H or C-6-H), 7.32 (2H, br s, exchanged with D$_2$O,—SO$_2$NH$_2$), 7.42 (2H, t, J=8.4 Hz. C-3'-H and C-5'-H or C-2'-H and C-6'-H), 7.69 (2H, d, J=8.4 Hz, C-2'-H and C-6'-H or C-3'-H and C-5'-H), 8.31 (1H, s, C-2-H), 9.53 (1H, s, C-7-OH) and 12.9 (1H, s, C-5-OH). MS: m/z (+ve ion FAB in m- NBA, rel. intensity) 350.0 [100, (M+H)$^+$], 271.1 [15, (M+H—SO$_2$NH$_2$)$^+$]. MS: m/z (−ve on FAB in m- NBA, rel. intensity) 347.9 [100, (M−H)$^-$], 269.0 [20, (M−H—SO$_2$NH$_2$)$^-$]. Acc. MS: m/z (FAB)$^+$ 350.0347 $C_{15}H_{12}NO_7S$ requires 350.0335. Found C, 51.0; H, 3.16; N, 3.90; $C_{15}H_{11}NO_7S$ requires C, 51.58; H, 3.17; N, 4.01%.

Isoflavone-4',7-O,O-Disulphamate (13)

4',7-Dihydroxy isoflavone (0.45 g, 1.77 mmol) upon sulphamoylation gave a crude product (0.769 g) which was fractionated on silica (200 g) with chloroform/acetone (4:1), and upon evaporation the second fraction gave a pale white residue (0.553 g, 72%) which was recrystallized in acetone/hexane (1:2) to give the compound (13) as white crystals (0.327 g); m.p.>195° C. (dec.); $R_f$=0.21 and 0.40 for chloroform/acetone 4:1 and 2:1 respectively; $v^{max}$ (KBr) 3400 (—NH$_2$), 1640 (C=O), 1360 (—SO$_2$N—) cm$^{-1}$. $\delta_H$ (DMSO-d$_6$), 7.37 (2H, d, J=8.8 Hz, C-3'-H and C-5'-H or C-2'-H and C-6'-H, 7.42 (1H, dd, J$_{C-6-H, C-8-H}$=2.2 Hz, J$_{C-6-H, C-5-H}$=8.8 Hz, C-6-H), 7.7 (2H, d, J=8.8 Hz, C-2'-H and -6'-H or C-3'-H and C-5'-H), 8.09 (2H, br s, exchanged with D$_2$O, —OSO$_2$NH$_2$), 8.24 (1H, d, J=8.8 Hz, C-5-H, 8.36 (2H, br s, exchanged with D$_2$O, —OSO$_2$NH$_2$), 8.63 (1H, s, C-2-H). MS: m/z (+ve ion FAB in m- NBA, rel. intensity) 412.9 [100, (M+H)$^+$], 334.0 [25, (M+H—SO$_2$NH$_2$)$^+$], 255.1 [20, (M+H—SO$_2$NH$_2$)$^+$]. MS: m/z (−ve ion FAB in m-NBA, rel. intensity) 410.9 [100, (M−H)$^-$], 332.0 [70, (M−H—SO$_2$NH$_2$)$^-$], 253.0 [30, (M−H—SO$_2$NH$_2$)$^-$]. Acc. MS: m/z (FAB)$^+$ 413.0119 C$_{15}$H$_{13}$N$_2$O$_8$S$_2$ requires 413.0113. Found C, 44.0; H, 2.94; N, 6.62; C$_{15}$H$_{12}$N$_2$O$_8$S$_2$ requires C, 43.69; H, 2.93; N, 6.79%.

Assay of inhibition of Sulphatase and Aromatase Activities

Sulphatase inhibition was assessed using placental microsome (100,000 g) preparations or intact MCF-7 breast cancer ells as described previously [29,30]. Placental microsomes were incubated with $^3$H E1S, adjusted to 20 µM with unlabelled substrate, in the absence or presence of inhibitor.

Placental microsomes were also used to assess the aromatase inhibitory properties of the flavanoid sulphamates using a tritiated water release assay[37]. Further placental microsomes (200 µl) were incubated with [1β-$^3$H] androstenedione, 60 nM and 1 mM NADPH in the absence or presence of inhibitor.

Inhibition of Sulphatase and Aromatase Activities

Inhibition of oestrone sulphatase and aromatase activities in placental microsomes by the flavanoid sulphamate derivatives is shown in the Table below.

| COMPOUND | CONCENTRATION µM | % INHIBITION Sulphatase | % INHIBITION Aromatase |
| --- | --- | --- | --- |
| Flavone-6-sulphamate | 1 | 26.8 | 1 |
|  | 10 | 89.5 | 6.5 |
| Flavone-7-sulphamate | 1 | — | 55 |
|  | 10 | — | 86 |
|  | 50 | 56.3 |  |
|  | 100 | 75.3 |  |
| 5-hydroxy flavone-7-sulphamate | 1 | 8 | 5 |
|  | 10 | 21 | 76 |
| 5,7-dihydroxy flavanone 4'-sulphamate | 0.1 | 30.4 | Not tested |
|  | 1 | 79.1 | Not tested |
|  | 10 | 98.1 | Not tested |
| 5-hydroxy-4'-methoxy-isoflavone-7-sulphamate | 1 | 1 | 2 |
|  | 10 | 50.6 | 5 |

From the results, it can be seen that potent inhibition of sulphatase and aromatase activities was detected. For sulphatase inhibition this ranged from 21% at 10 µM by 5-hydroxy flavone-7-sulphamate, to 98% by 5,7-dihydroxy flavanone-4'-sulphamate at 10 µM. Potent aromatase inhibition was also achieved ranging from 6.5% by flavone-6-sulphamate at 10 µM to 86% by flavone-7-sulphamate at 10 µM.

Further in vitro Testing

The following Table presents in vitro data for three isoflavones that were tested.

| | IN VITRO ACTIVITY | | |
| --- | --- | --- | --- |
| | | % Inhibition | |
| Compound | Concentration (µM) | MCF-7 Cells | Placental Microsomes |
| Isoflavone 5-hydroxy-4',7-bissulphamate | 0.1 | 28 | nd |
|  | 1.0 | 90 | nd |
|  | 10.0 | 99 | 93 |
| Isoflavone 5,7-dihydroxy-4'-sulphamate | 0.1 | 23 | nd |
|  | 1.0 | 83 | nd |
|  | 10.0 | 99 | 75 |
| Isoflavone-4',7-bissulphamate | 0.1 | 89 | nd |
|  | 1.0 | 99 | nd |
|  | 10.0 | 99 | 99 | nd = not done

In Vivo Testing

Figure 11:
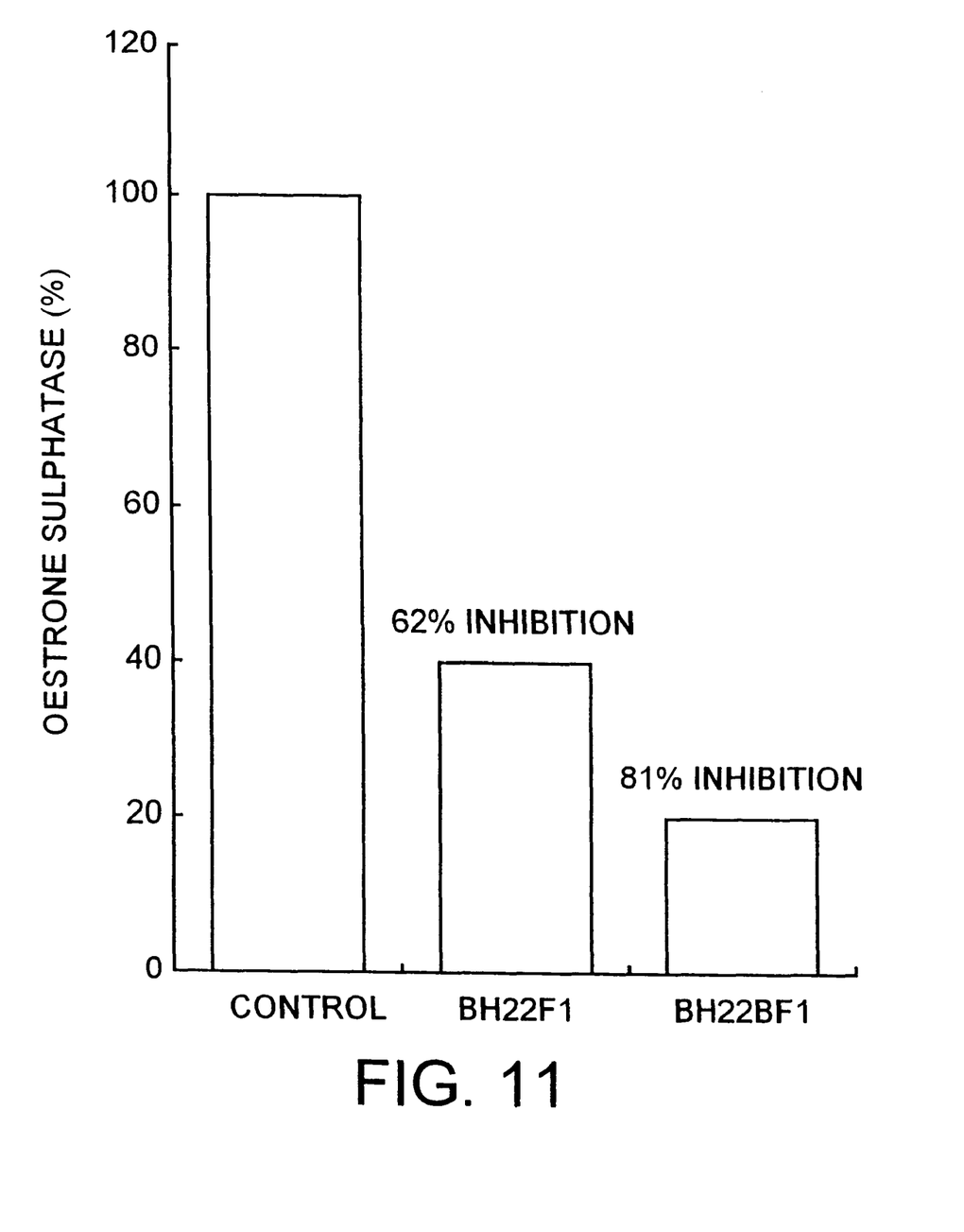
FIG. 11 presents a graphy of oestrone sulphatase percent inhibition.

FIG. 11 presents in vivo inhibition of oestrone sulphatase activity in rat liver for two isoflavones according to the present invention. In this regard, BH22F1=5-hydroxy isoflavone-4',7-bissulphamate, BH22BF1=5,7-dihydroxy isoflavone-4'-sulphamate. Compounds were administered as a single 10 mg/Kg dose. Oestrone sulphatase activity was assayed in tissue samples obtained 24 h after drug administration.

Other modifications of the present invention will be apparent to those skilled in the art.

REFERENCES (1) Santner, S. J.; Feil, P. D.; Santen, R. J. In situ oestrogen production via the oestrone sulphatase pathway in breast tumors: relative importance vs. the aromatase pathway. *J. Clin. Endocrinol. Metab.* 1984, 59, 29–33.

(2) Yamamoto, T.; Kitawaki, J.; Urabe, M.; Honjo, H.; Tamura, T.; Noguchi, T.; Okada, H.; Sasaki, H.; Tada, A.; Terashima, Y.; Nakamura, J.; Yoshihama, M. Oestrogen productivity of endometrium and endometrial cancer tissue—influence of aromatase on proliferation of endometrial cancer cells. *J. Steroid Biochem. Mol. Biol.* 1993, 44, 463–468.

(3) Santen, R. J.; Santner, S. J.; Davis, B.; Veldhuis, J.; Samojilik, E.; Ruby, E. Aminogluthethimide inhibits extraglandular oestrogen production in post-menopausal women with breast carcinoma. *J. Clin. Endocrinol. Metab.* 1978, 47, 1257–1265.

(4) Reed, M. J.; Lai, L. C.; Owen, A. M.; Singh, A.; Coldham, N. G.; Purohit, A.; Ghilchik, M. W.; Shaikh, N. A.; James, V. H. T. Effect of treatment with 4-hydroxy-androstenedione on the peripheral conversion of androstenedione to oestrone and in vitro tumour aromatase activity in postmenopausal women with breast cancer. *Cancer Res.* 1990, 50, 193–196.

(5) Ruder, H. J.; Loriaux, D. L.; Lipsett, M. . Oestrone sulphate: production rate and metabolism in man. *J. Clin. Invest.* 1972 51, 1020–1023.

(6) James, V. H. T.; McNeill, J. M.; Lai, L. .; Newton. C. J.; Ghilchik, M. W.; Reed, M. J. Aromatase activity in normal breast and breast rumor tissues: in vivo and in vitro studies. *Steroids* 1987, 50, 269–79.

(7) Howarth, N. M.; Purohit, A.; Reed, M. J.; Potter, B. V. L. Oestrone sulphamates: potent inhibitors of oestrone sulphatase with therapeutic potential. *J. Med. Chem.* 1994, 37, 219–221.

(8) Purohit, A.; Williams, G. J.; Howarth, N. M.; Potter, B. V. L.; Reed, M. J. Inactivation of steroid sulphatase by an active ite-directed inhibitor, oestrone-3-O-sulphamate. *Biochemistry* 1995, 34, 11508–11 14.

(9) Purohit, A.; Dauvois, S.; Parker, M. G. Potter, B. V. L.; Williams, G. J.; Reed, M. J. The hydrolysis of oestrone sulphate and dehydroepiandrosterone sulphate by human steroid sulphatase expressed in transfected COS-1 cells. *J. Steroid Biochem. Mol. Biol.* 1994, 50, 101–104.

(10) Dauvois, S.; Labrie, F. Androstenedione and androst-5-ene-3β,17β-diol stimulate DMBA-induced rat mammary tumours—role of aromatase. *Breast Cancer Res. Treat.* 1989, 13, 61–69.

(11) Purohit, A.; Williams, G. J.; Roberts, C. J.; Potter, B. V. L.; Reed. M. J. In vivo inhibition of oestrone sulphatase and dehydroepiandrosterone sulphatase by oestrone-3-O-sulphamate. *Int. J. Cancer* 1995, 63, 106–111.

(12) Woo, L. W. L.; Lightowler, M.; Purohit, A.; Reed, M. J.; Potter, B. V. L. Heteroatom-substituted analogues of the active-site directed inhibitor oestra-1,3,5(10)-trien-17-one-3-sulphamate inhibit oestrone sulphatase by a different mechanism. *J. Steroid Biochem. Mol. Biol.* 1996 (in press).

(13) Elger, W.; Schwarz, S.; Hedden, A.; Reddersen, G.; Schneider, B. Sulphamates of various oestrogens—prodrugs with increased systemic and reduced hepatic oestrogenicity at oral application. *J. Steroid Biochem. Mol. Biol.* 1995, 55, 395–403.

(14) Li, P. K; Rhodes, M. E.; Jagannathan, S; Johnson, D. A. Memory enhancement mediated by the steroid sulphatase inhibitor oestrone 3-O-sulphamate. *J. Endocrinol.* 1995, 144, Abstr. P155.

(15) Daynes, R. A.; Araneo, B. A.; Dowell, T. A.; Huang, K.; Dudley, D. Regulation of murine lymphokine production in vivo. 3. The lymphoid tissue micro-environment exerts regulatory influences over T-helper cell function. *J. Exp. Med.* 1990, 171, 979–996.

(16) Rook, G. A. W.; Hernandez-Pando, R.; Lightman, S. Hormones, peripherally activated prohormones and regulation of the TH1/TH2 balance. *Immunol. Today* 1994, 15, 301–303.

(21) James & Reed (1980) Prog Cancer Res her 14: 471–487.

(22) James et al (1987) Steroids 50: 269–279.

(23) Reed et al (1994) Drugs for the Future 9: 673–680.

(24) Santner et al (1984) J Clin Endocr Meta 59: 29–33.

(25) Yamamoto et al (1993) J Steroid Biochem Molec Biol 44: 463–468.

(26) Poulin & Labrie (1986) Cancer Res 46: 933–4937.

(27) Dauvois & Labrie (1989) Breast Cancer Res Treat 13: 61–69.

(28) Purohit et al (1994) J Steroid Biochem Mol Biol 50: 101–104.

(29) Howarth et al (1994) J Med Chem 37: 219–221.

(30) Purohit et al (1995) Biochemistry 34: 11508–11514.

(31) Purohit et al (1995) Inc J Cancer 62: 106–111.

(32) Svenstrup et at (1994) Eur J Cancer 30A: 1254–1258.

(33) Johnston et al (1994) Cancer Res 54: 5875–5881.

(34) Dowsett et al (1994) Eur J Cancer 30A 1453–1458.

(35) Kellis et al (1986) Biochem Pharmacol 35: 2887–2891.

(36) Campbell & Kurzer (1993) J Steroid Biochem Molec Biol 46: 381–388.

(37) Newton et al (1986) J Steroid Biochem 24: 1033–1039.

(38) Kellis et al (1986) Biochem Pharmacol 35: 2887

What is claimed is:

1. A sulphamate compound of the general formula IV, or V, or VI:

IV

V

VI wherein $R_1$–$R_{12}$ are independently selected from H, OH, a halogen, an amine, an amide, a sulphonamine, a sulphonamide, a saturated or unsaturated $C_{1-10}$ alkyl, an aryl group, a saturated or unsaturated $C_{1-10}$ ether, and a saturated or unsaturated $C_{1-10}$ ester; and wherein at least one of $R_1$–$R_{12}$ is a sulphamate group.

2. A sulphamate compound of the general formula VII, or VIII, or IX

VII

VIII wherein $R_1$–$R_4$ are independently selected from H, OH, a halogen, an amine, an amide, a sulphonamine, a sulphonamide, a saturated or unsaturated $C_{1-10}$ alkyl, an aryl group, a saturated or unsaturated $C_{1-10}$ ether, and a saturated or unsaturated $C_{1-10}$ ester; and wherein at least one of $R_1$–$R_4$ is a sulphamate group.

3. A compound according to claim 1, wherein the ring having substituent $R_1$ is a first ring and the ring having substituent $R_4$ is a second ring and any one of the first and second rings is bound thereto a sulphamate group.

4. A compound according to claim 2, wherein the ring having substituent $R_1$ is a first ring and the ring having substituent $R_4$ is a second ring and any one of the first and second rings is bound thereto a sulphamate group.

5. A compound according to claim 1 wherein the sulphamate group has the general formula $OSO_2NR_{13}R_{14}$ wherein $R_{13}$ and $R_{14}$ are independently selected from H, OH, a halogen, a saturated or unsaturated $C_{1-10}$ alkyl, an aryl group, a saturated or unsaturated $C_{1-10}$ ether, and a saturated or unsaturated $C_{1-10}$ ester.

6. A compound according to claim 2 wherein the sulphamate group has the general formula $OSO_2NR_{13}R_{14}$ wherein $R_{13}$ and $R_{14}$ are independently selected from H, OH, a halogen, a saturated or unsaturated $C_{1-10}$ alkyl, an aryl group, a saturated or unsaturated $C_{1-10}$ ether, and a saturated or unsaturated $C_{1-10}$ ester.

7. A compound according to claim 1 wherein the sulphamate group has the general formula $OSO_2NR_{13}R_{14}$ wherein $R_{13}$ and $R_{14}$ are independently selected from H, OH, a halogen, a saturated or unsaturated $C_{1-10}$ alkyl, an aryl group, a saturated or unsaturated $C_{1-10}$ ether, and a saturated or unsaturated $C_{1-10}$ ester; and, $R_1$–$R_{12}$ are independently selected from H, OH, $OSO_2NR_{13}R_{14}$, and O—$CH_3$.

8. A compound according to claim 5 wherein $R_{13}$ and $R_{14}$ are H.

9. A compound according to claim 6 wherein $R_{13}$ and $R_{14}$ are H.

10. A compound according to claim 7 wherein $R_{13}$ and $R_{14}$ are H.

11. A compound according to claim 1 wherein the sulphamate group is on $R_4$.

12. A compound according to claim 2 wherein the sulphamate group is on $R_4$.

13. A compound according to claim 5 wherein the sulphamate group is on $R_4$.

14. A compound according to claim 6 wherein the sulphamate group is on $R_4$.

15. A compound according to claim 7 wherein the sulphamate group is on $R_4$.

16. A compound according to claim 8 wherein the sulphamate group is on $R_4$.

17. A compound according to claim 9 wherein the sulphamate group is on $R_4$.

18. A compound according to claim 10 wherein the sulphamate group is on $R_4$.

19. A pharmaceutical composition comprising a compound according to any one of claims 1, 2 or 3 to 8; and a pharmaceutically acceptable carrier, excipient or diluent.

20. A composition for inhibiting oestrone sulphatase activity and aromatase activity comprising a compound according to any one of claims 1, 2 or 3 to 18 and a pharmaceutically acceptable carrier, excipient or diluent.

21. A process for preparing a compound according to any one of claims 1, 2 or 3 to 18, comprising reacting a non-sulphamated compound of formula IV, or V, or VI, or VII, or VIII or IX, with a sulphamoylating agent to form the compound.

* * * * *